United States Patent
Mori et al.

(10) Patent No.: US 12,376,902 B2
(45) Date of Patent: Aug. 5, 2025

(54) BALLOON-TYPE ELECTRODE CATHETER AND METHOD OF ACTUATING BALLOON-TYPE ELECTRODE CATHETER

(71) Applicant: Japan Lifeline Co., Ltd., Tokyo (JP)

(72) Inventors: Kenji Mori, Tokyo (JP); Yohei Suzuki, Tokyo (JP)

(73) Assignee: JAPAN LIFELINE CO., LTD., Tokyo (JP)

(*) Notice: Subject to any disclaimer, the term of this patent is extended or adjusted under 35 U.S.C. 154(b) by 433 days.

(21) Appl. No.: 18/160,037

(22) Filed: Jan. 26, 2023

(65) Prior Publication Data

US 2023/0270491 A1    Aug. 31, 2023

(30) Foreign Application Priority Data

Feb. 28, 2022   (JP) .................................. 2022029640

(51) Int. Cl.
*A61B 18/14*       (2006.01)
*A61B 18/00*       (2006.01)
A61M 25/10         (2013.01)

(52) U.S. Cl.
CPC   *A61B 18/1492* (2013.01); *A61B 2018/00232* (2013.01); *A61M 2025/1004* (2013.01)

(58) Field of Classification Search
CPC ...... A61B 18/1492; A61B 2018/00232; A61B 2018/00029; A61B 2018/00166; A61B 2018/0022; A61B 2218/002; A61B 2018/00791; A61B 2018/00577; A61B 2018/00357; A61B 2018/00375; A61B 2018/00285; A61B 2018/00351; A61B 18/14; A61M 2025/1004; A61M 25/1002

USPC ........................................................ 606/41
See application file for complete search history.

(56) References Cited

U.S. PATENT DOCUMENTS

| | | | | |
|---|---|---|---|---|
| 4,961,738 | A | * | 10/1990 | Mackin ................ A61B 1/3137 600/116 |
| 2008/0132937 | A1 | * | 6/2008 | Hartley ............ A61B 17/12109 604/101.03 |
| 2015/0217093 | A1 | * | 8/2015 | Tsutsui .................. A61M 29/02 606/194 |
| 2015/0306359 | A1 | * | 10/2015 | Drasler ................ A61F 2/2433 606/191 |
| 2019/0015639 | A1 | * | 1/2019 | Wang ..................... A61L 29/16 |
| 2019/0015640 | A1 | * | 1/2019 | Wang ..................... A61L 29/06 |

(Continued)

FOREIGN PATENT DOCUMENTS

JP          201760825          3/2017

*Primary Examiner* — Linda C Dvorak
(74) *Attorney, Agent, or Firm* — MUNCY, GEISSLER, OLDS & LOWE, P.C.

(57) ABSTRACT

A balloon-type electrode catheter includes a catheter shaft including an outer shaft and an inner shaft, a balloon provided at a part including a distal end of the catheter shaft, and an electrode. The balloon includes an outer joining portion an inner joining portion, a distal end large diameter portion, a proximal end large diameter portion, a small diameter portion positioned between the two large diameter portions and being smaller in diameter than the two large diameter portions, a distal end inclined portion connecting the distal end large diameter portion and the small diameter portion, and a proximal end inclined portion connecting the proximal end large diameter portion and the small diameter portion. The electrode is exposed at at least the small diameter portion.

8 Claims, 9 Drawing Sheets

(56) References Cited

U.S. PATENT DOCUMENTS

| | | | |
|---|---|---|---|
| 2019/0344053 A1* | 11/2019 | Wang | B29D 22/023 |
| 2019/0374685 A1* | 12/2019 | Wang | A61L 29/16 |
| 2020/0038672 A1* | 2/2020 | Satake | A61N 1/403 |
| 2020/0215310 A1* | 7/2020 | Rentschler | A61B 1/00082 |
| 2020/0276417 A1* | 9/2020 | Rentschler | A61M 25/1029 |
| 2020/0398032 A1* | 12/2020 | Wang | A61M 5/007 |
| 2021/0113742 A1* | 4/2021 | Wang | A61M 25/10185 |
| 2023/0001163 A1* | 1/2023 | Wang | A61M 25/1002 |
| 2023/0066969 A1* | 3/2023 | Tsukamoto | A61B 18/082 |

* cited by examiner

BALLOON-TYPE ELECTRODE CATHETER AND METHOD OF ACTUATING BALLOON-TYPE ELECTRODE CATHETER

TECHNICAL FIELD

The present disclosure relates to a balloon-type electrode catheter and a method of actuating the balloon-type electrode catheter.

BACKGROUND ART

Patients suffering from heart failure, pulmonary hypertension, and the like may have a high blood pressure in the atria. A known treatment for suppressing the rise in the atrial pressure includes a shunt surgery in which a shunt (through hole) for releasing the atrial pressure is formed in the atrial septum. In the shunt surgery, a peripheral edge portion of the through hole may be thermally ablated using an ablation catheter including an electrode at a distal end so that the through hole is preserved for a predetermined period of time (see, for example, Patent Literature 1).

CITATION LIST

Patent Literature

Patent Literature 1: JP 2017-60825 A

SUMMARY OF INVENTION

Technical Problem

When the peripheral edge portion of the shunt is thermally ablated using the ablation catheter described above, the position of the electrode is desired to be maintained during the ablation for more reliable thermal ablation of the peripheral edge portion.

The present disclosure has been made in view of such circumstances, and an object thereof is to provide a technique of suppressing displacement of an electrode provided at a catheter.

Solution to Problem

An aspect of the present disclosure is a balloon-type electrode catheter. This balloon-type electrode catheter includes a catheter shaft including an outer shaft having a tubular shape and an inner shaft housed in the outer shaft in a state in which the inner shaft is displaceable relative to the outer shaft in an axial direction of the outer shaft, the catheter shaft being insertable into a body, a balloon provided at a part including a distal end of the catheter shaft, the balloon being inflatable with a fluid supplied from a part including a proximal end of the catheter shaft, and an electrode disposed on a surface of the balloon. The balloon includes an outer joining portion joined to the outer shaft and an inner joining portion joined to the inner shaft at a position displaced from the outer joining portion in the axial direction, and the balloon in an inflated state includes a distal end large diameter portion, a proximal end large diameter portion positioned closer to the proximal end of the catheter shaft than the distal end large diameter portion is, a small diameter portion positioned between the distal end large diameter portion and the proximal end large diameter portion and being smaller in diameter than the two large diameter portions, a distal end inclined portion connecting the distal end large diameter portion and the small diameter portion, and a proximal end inclined portion connecting the proximal end large diameter portion and the small diameter portion. The electrode is exposed at at least the small diameter portion. After the balloon is inflated by inflow of the fluid, the outer shaft and the inner shaft are displaced relative to each other, and thus the balloon deforms such that the distal end inclined portion and the proximal end inclined portion approach each other.

Another aspect of the present disclosure is a method of actuating a balloon-type electrode catheter including a balloon provided with an electrode, the balloon being provided at a part including a distal end of a catheter shaft. This method of actuating the balloon-type electrode catheter includes causing a fluid to flow into the balloon to inflate the balloon in a dumbbell shape, deforming the balloon such that a distal end portion and a proximal end portion of the balloon approach each other along an axial direction of the catheter shaft, and energizing the electrode.

Any combination of the above components and conversions of expressions of the present disclosure between a method, a device, a system, and the like are also effective as aspects of the present disclosure.

Advantageous Effects of Invention

According to the present disclosure, displacement of an electrode provided at a catheter can be suppressed.

DESCRIPTION OF EMBODIMENTS

Figure 1:
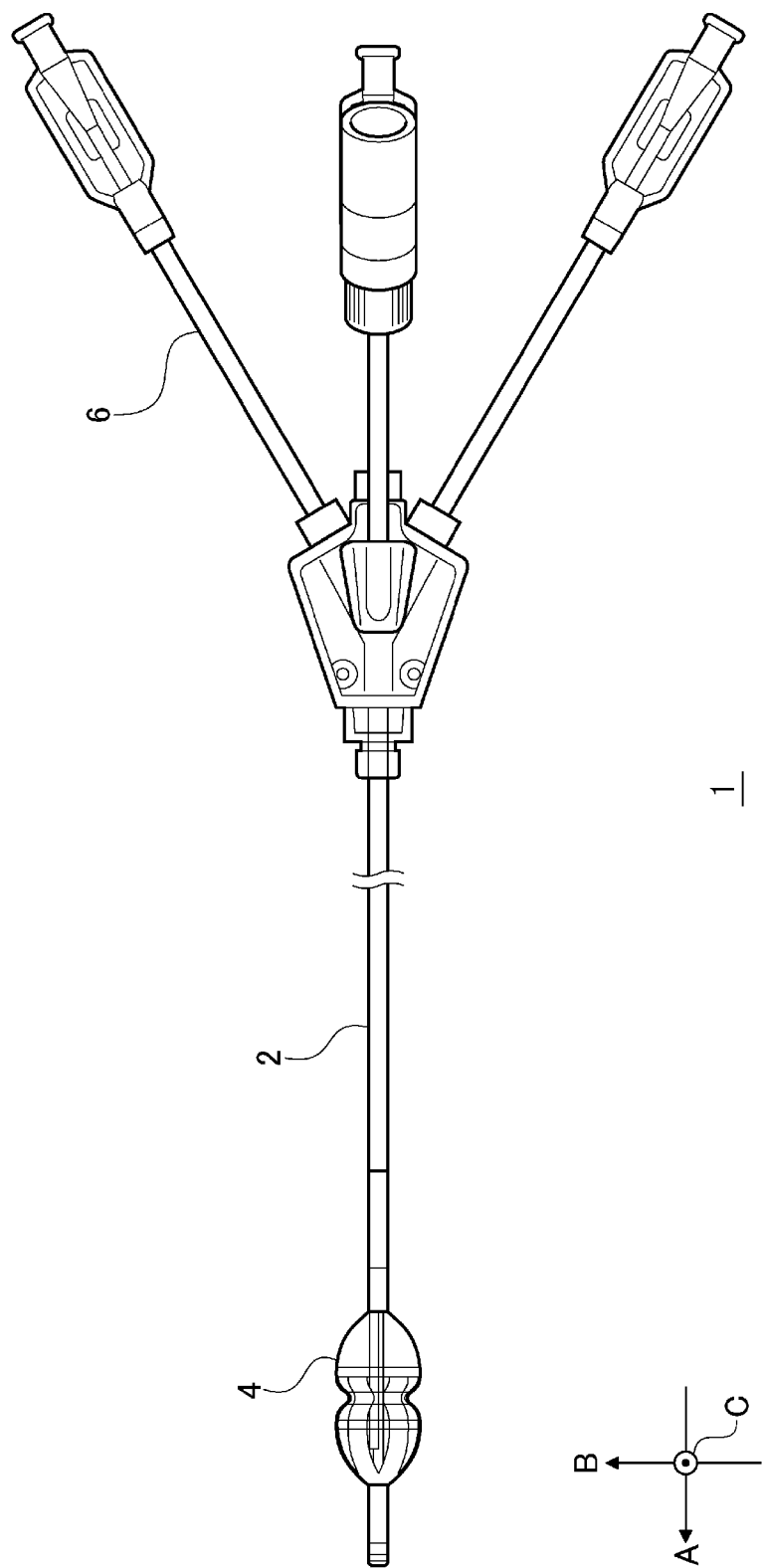
FIG. 1 is a plan view of a balloon-type electrode catheter according to an embodiment.

The present disclosure will be described below based on preferred embodiments with reference to the drawings. The embodiments are illustrative and are not intended to limit the present disclosure. Not all features or combinations of the features described in the embodiments are essential to the present disclosure. The same or similar components, members, and processing operations illustrated in the drawings are denoted by the same reference numerals, and redundant descriptions are omitted as appropriate. The scales and shapes of the parts illustrated in each drawing are set for convenience to facilitate the explanation and should not be construed in a limited manner unless otherwise specified. When the terms "first", "second", and the like are used in the specification or claims, these terms do not mean any order or importance unless otherwise specified and are used for distinguishing a configuration from other configurations. Furthermore, some of the members that are not critical in describing the embodiments in the drawings are omitted in illustration.

FIG. 1 is a plan view of a balloon-type electrode catheter 1 according to an embodiment. The balloon-type electrode catheter 1 includes a catheter shaft 2, a balloon 4, and a handle 6. The catheter shaft 2 is a long tubular member. The length of the catheter shaft 2 is, for example, 600 mm to 1800 mm. The balloon 4 is provided at a part including the distal end of the catheter shaft 2. The handle 6 is provided at a part including the proximal end of the catheter shaft 2. Hereinafter, a part of the balloon-type electrode catheter 1 or the catheter shaft 2 where the balloon 4 is provided is simply referred to as "distal end part", and a part where the handle 6 is provided is simply referred to as "proximal end part". The catheter shaft 2 is inserted into the body from the distal end part. The balloon 4 is thus fed into the body. The handle 6 is disposed outside the body and operated by a practitioner.

Figure 2:
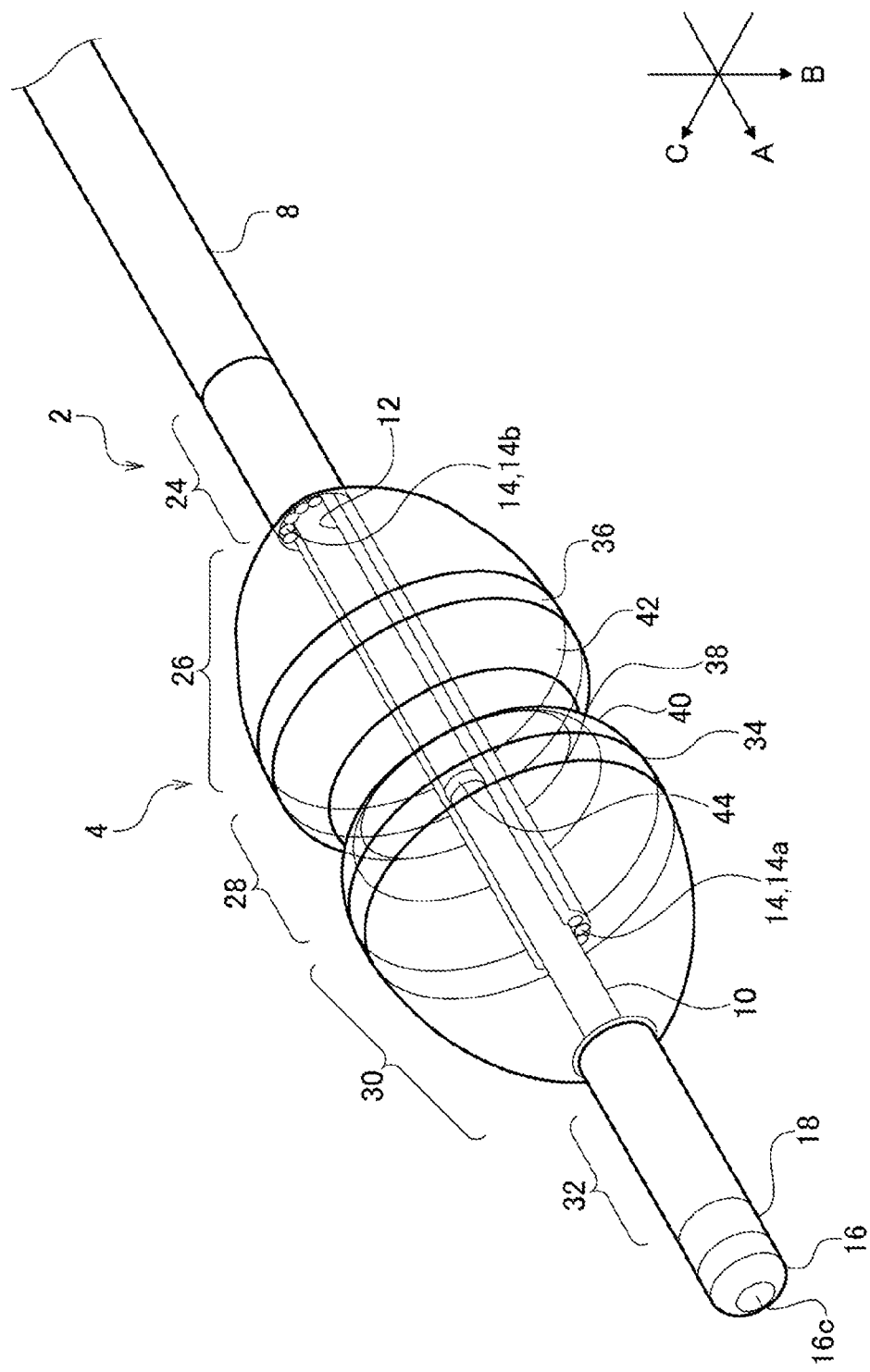
FIG. 2 is an enlarged perspective view of a part including a distal end of the balloon-type electrode catheter.
Figure 3:
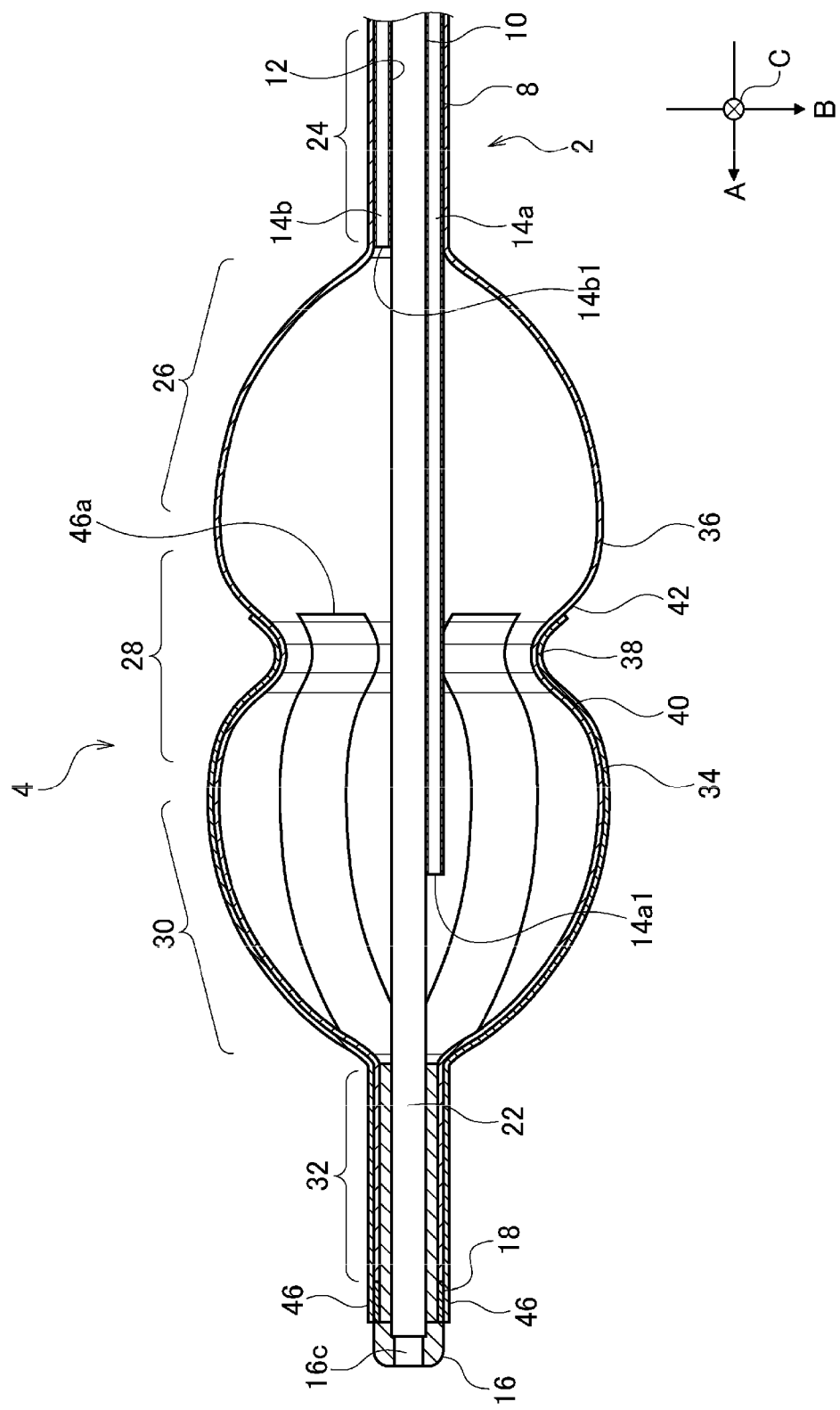
FIG. 3 is an enlarged sectional view of the part including the distal end of the balloon-type electrode catheter.
Figure 4:
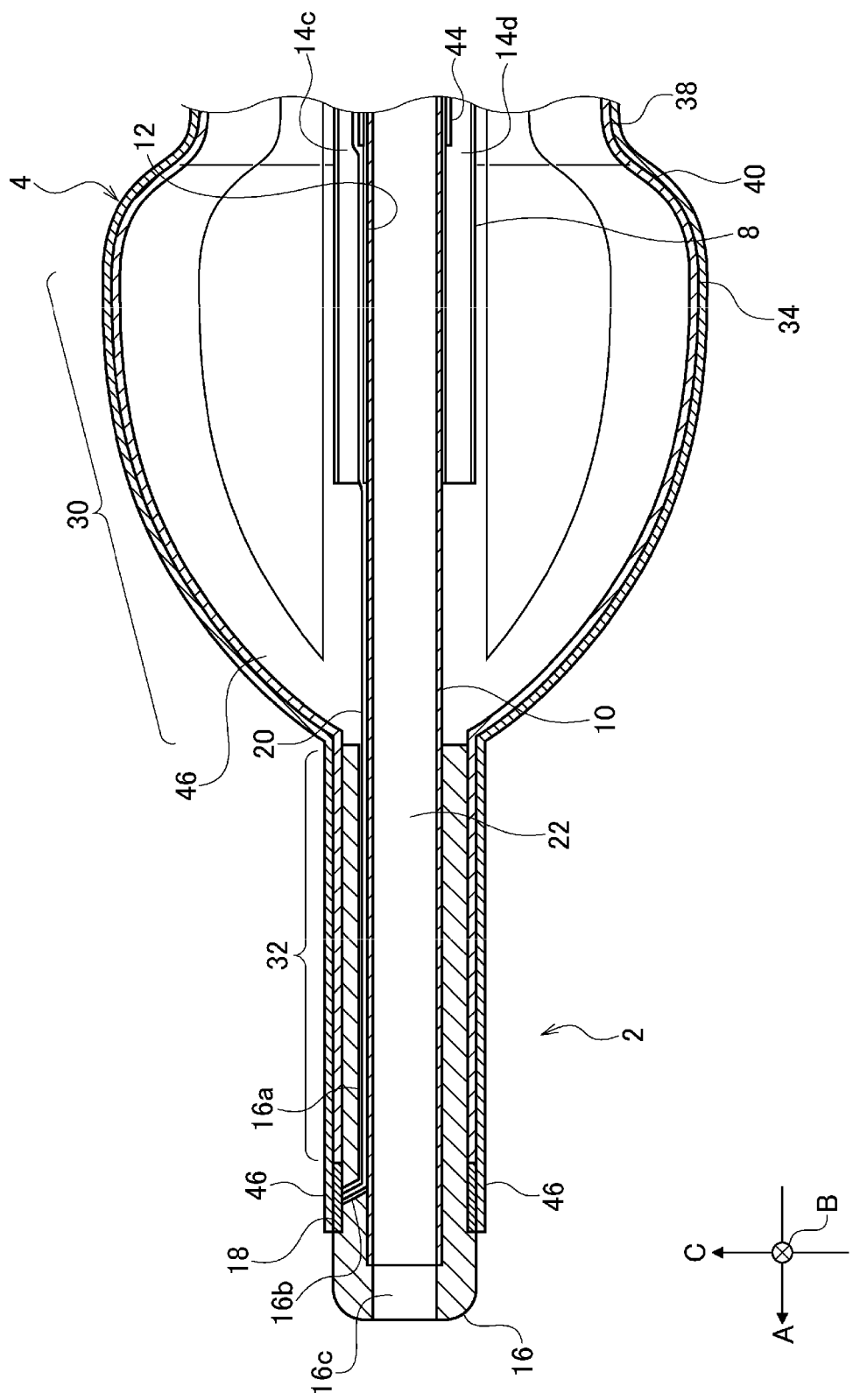
FIG. 4 is an enlarged sectional view of the part including the distal end of the balloon-type electrode catheter.

FIG. 2 is an enlarged perspective view of the distal end part of the balloon-type electrode catheter 1. FIG. 3 is an enlarged sectional view of the distal end part of the balloon-type electrode catheter 1. FIG. 4 is an enlarged sectional view of the distal end part of the balloon-type electrode catheter 1. FIGS. 2 to 4 illustrate the balloon 4 in an inflated state. For convenience of explanation, some members are omitted in each of the drawings.

As illustrated in FIGS. 2 and 3, the catheter shaft 2 includes an outer shaft 8 and an inner shaft 10. The outer shaft 8 and the inner shaft 10 are made of a known flexible material such as a resin including a polyolefin or a polyamide. The outer shaft 8 is tubular, and houses therein the inner shaft 10. The inner shaft 10 is housed in the outer shaft 8 in a state in which the inner shaft 10 is displaceable relative to the outer shaft 8 in the axial direction of the outer shaft 8.

The outer shaft 8 of the present embodiment has a multi-lumen structure. Specifically, the outer shaft 8 includes a main lumen 12 extending in a region overlapping the central axis of the outer shaft 8 and a plurality of sub-lumens 14 disposed around the main lumen 12. The main lumen 12 and each of the sub-lumens 14 extend from the distal end part to the proximal end part of the outer shaft 8. The inner shaft 10 is housed in the main lumen 12. Among the plurality of sub-lumens 14, some constitute a supply lumen 14a, some other constitute a discharge lumen 14b, some other constitute a lead-wire lumen 14c, and some other constitute a sensor lumen 14d. Functions of each of the sub-lumens 14 will be described in detail later.

The inner shaft 10 includes a distal end portion positioned closer to the distal end than the balloon 4 is. The distal end portion protrudes from the outer shaft 8. This distal end portion is covered with a cap-like distal end tip 16. The distal end tip 16 is made of a known resin material like the catheter shaft 2. The distal end tip 16 and the inner shaft 10 are joined to each other by fusion as an example. A connecting member 18 is fitted to a part of the outer peripheral surface of the distal end tip 16. As an example, the connecting member 18 has a ring shape, and is made of a metal material such as platinum or iridium. Thus, the connecting member 18 has conductivity. The distal end tip 16 and the connecting member 18 are disposed closer to the distal end than the balloon 4 is.

As illustrated in FIG. 4, the inner peripheral surface of the distal end tip 16 is provided with a groove 16a extending from the proximal end toward the distal end of the distal end tip 16. The distal end tip 16 is also provided with a lead-wire through hole 16b extending from the distal end of the groove 16a toward the connecting member 18. The balloon-type electrode catheter 1 includes a lead wire 20 extending from the proximal end part toward the distal end part of the catheter shaft 2. The lead wire 20 passes through the lead-wire lumen 14c from the proximal end part of the catheter shaft 2 and reaches the distal end tip 16. The lead wire 20 that reaches the distal end tip 16 passes through the groove 16a and the lead-wire through hole 16b and is electrically connected to the connecting member 18. The connecting member 18 and the lead wire 20 are joined to each other by welding as an example. An opening of the groove 16a facing the inside of the balloon 4 is sealed with an adhesive or the like. The proximal end of the lead wire 20 is connected to an external power supply device via the handle 6.

The inner shaft 10 of the present embodiment has a single lumen structure. The inner shaft 10 includes a wire lumen 22 extending in a region overlapping the central axis of the inner shaft 10. The distal end tip 16 includes a wire through hole 16c at a position overlapping the wire lumen 22 in the axial direction of the catheter shaft 2. A guide wire GW (see FIG. 8A and the like) passes through the wire lumen 22 and the wire through hole 16c.

The balloon 4 is inflatable with a fluid supplied from the proximal end part of the catheter shaft 2. The fluid is, for example, saline. The balloon 4 is made of a known flexible material including a resin such as a polyolefin or a polyamide. As illustrated in FIGS. 2 and 3, the balloon 4 includes an outer joining portion 24, a proximal end inflatable portion 26, and a constricted portion 28, a distal end inflatable portion 30, and an inner joining portion 32 in this order from the proximal end part of the catheter shaft 2.

The outer joining portion 24 has a tubular shape with approximately the same diameter as the outer shaft 8 and surrounds the outer peripheral surface of the outer shaft 8 in a region adjacent to the balloon 4. The outer joining portion 24 and the outer shaft 8 are joined to each other by fusion as an example. Thus, one end of the balloon 4 is joined to the outer shaft 8. Note that in the present embodiment, the outer peripheral surface of the outer shaft 8 in a region adjacent to the balloon 4 is thinned by an amount corresponding to the thickness of the outer joining portion 24. Thus, in a state where the region and the outer joining portion 24 are joined, the outer peripheral surface of the outer joining portion 24 and the outer peripheral surface of the outer shaft 8 are flush with each other.

The inner joining portion 32 has a tubular shape with approximately the same diameter as the distal end tip 16 and surrounds the outer peripheral surface of a part of the distal end tip 16 closer to the proximal end than the connecting member 18 is. The inner joining portion 32 and the distal end tip 16 are joined to each other by fusion as an example. Thus, the other end of the balloon 4 is joined to the inner shaft 10 at a position displaced from the joining portion (outer joining portion 24) between the balloon 4 and the outer shaft 8 in the axial direction of the catheter shaft 2. Note that in the present embodiment, in a state where the distal end tip 16 and the inner joining portion 32 are joined, the outer peripheral surface of the inner joining portion 32 and the outer peripheral surface of the connecting member 18 are flush with each other.

The proximal end inflatable portion 26 extends between the outer joining portion 24 and the constricted portion 28 and includes a portion having the largest diameter of the balloon 4. The distal end inflatable portion 30 extends between the inner joining portion 32 and the constricted portion 28 and includes a portion having the largest diameter of the balloon 4. The constricted portion 28 is a portion that is between the proximal end inflatable portion 26 and the distal end inflatable portion 30 and that is recessed radially across the entire area of the balloon 4 in a circumferential direction (direction around the axis of the catheter shaft 2). Because of the proximal end inflatable portion 26, the constricted portion 28, and the distal end inflatable portion 30, the inflated balloon 4 has a dumbbell shape.

The balloon 4 in an inflated state includes a distal end large diameter portion 34, a proximal end large diameter portion 36, and a small diameter portion 38. The proximal end large diameter portion 36 is positioned closer to the proximal end of the catheter shaft 2 than the distal end large diameter portion 34 is. The small diameter portion 38 is positioned between the distal end large diameter portion 34 and the proximal end large diameter portion 36. The distal end large diameter portion 34 and the proximal end large diameter portion 36 are larger in diameter than the small diameter portion 38. The small diameter portion 38 is smaller in diameter than the two large diameter portions. For example, the diameter of the distal end large diameter portion 34 and the proximal end large diameter portion 36 is from 9 mm to 15 mm, and the diameter of the small diameter portion 38 is from 6 mm to 12 mm.

The balloon 4 also includes a distal end inclined portion 40 and a proximal end inclined portion 42. The distal end inclined portion 40 is a portion connecting the distal end large diameter portion 34 and the small diameter portion 38 and is inclined from the distal end large diameter portion 34 toward the small diameter portion 38 to approach the catheter shaft 2. The proximal end inclined portion 42 is a portion connecting the proximal end large diameter portion 36 and the small diameter portion 38 and is inclined from the proximal end large diameter portion 36 toward the small diameter portion 38 to approach the catheter shaft 2.

In the balloon 4 of the present embodiment, the distal end large diameter portion 34 is disposed at the distal end inflatable portion 30, the proximal end large diameter portion 36 is disposed at the proximal end inflatable portion 26, and the small diameter portion 38, the distal end inclined portion 40, and the proximal end inclined portion 42 are disposed at the constricted portion 28. As an example, the distal end large diameter portion 34 and the proximal end large diameter portion 36 are portions having the largest diameter in the balloon 4. The small diameter portion 38 is a portion having the smallest diameter in the constricted portion 28. Note that the proximal end inflatable portion 26 and the distal end inflatable portion 30 have mutually inverted shapes relative to the constricted portion 28, but the shapes of the two inflatable portions are not limited thereto. For example, only one of the inflatable portions may include a portion having the largest diameter of the balloon 4. The distal end large diameter portion 34 and the proximal end large diameter portion 36 may have different diameters.

The supply lumen 14a and the discharge lumen 14b of the outer shaft 8 are connected to the inside of the balloon 4. The supply lumen 14a is a lumen for causing a fluid to flow into the balloon 4. The supply lumen 14a includes, in the balloon 4, a supply port 14a1 for causing a fluid to flow into the balloon 4. The proximal end of the supply lumen 14a is connected to an external fluid supply/discharge device via the handle 6. The fluid sent from the fluid supply/discharge device passes through the supply lumen 14a and is ejected into the balloon 4 from the supply port 14a1. Thus, the balloon 4 can be inflated.

The discharge lumen 14b is a lumen for discharging gas in the balloon 4. The discharge lumen 14b includes, in the balloon 4, a discharge port 14b1 for causing gas to flow out of the balloon 4. The proximal end of the discharge lumen 14b is connected to the outside via the handle 6. The discharge lumen 14b is used during an air removal process prior to the use of the balloon-type electrode catheter 1, for example. That is, a fluid is supplied into the balloon 4 through the supply lumen 14a from the fluid supply/discharge device. The fluid supplied into the balloon 4 flows into the discharge lumen 14b from the discharge port 14b1 along with the gas in the balloon 4 and is discharged to the outside through the discharge lumen 14b. Note that the gas in the supply lumen 14a, as well as the gas in the balloon 4, can be discharged to the outside. To deflate the balloon 4 during the use of the balloon-type electrode catheter 1, the fluid is discharged from the inside of the balloon 4 through the supply lumen 14a.

In the present embodiment, the supply port 14a1 is positioned closer to the distal end of the catheter shaft 2 than the discharge port 14b1 is. This can cause a fluid to flow into the balloon 4 from a position closer to the distal end of the catheter shaft 2 and discharge gas from a position closer to the proximal end of the catheter shaft 2. Thus, more reliable air removal can be performed. In the outer shaft 8 of the present embodiment, the distal end portion positioned in the balloon 4 is cut out partially in the circumferential direction. Specifically, a part of the distal end portion extending from the discharge lumen 14b is cut out. In the remaining part of the distal end portion, the supply lumen 14a extends. As a result, the supply port 14a1 is displaced to be closer to the distal end of the catheter shaft 2 than the discharge port 14b1 is.

As the distal end portion of the outer shaft 8 is cut out, a part of the inner shaft 10 is exposed inside the balloon 4. The exposed portion of the inner shaft 10 is provided with a contrast marker 44 at a position overlapping the small diameter portion 38 when viewed from the radial direction of the balloon 4 (the direction orthogonal to the axis of the catheter shaft 2). The practitioner can grasp the position of the balloon 4, and thus the position of the small diameter portion 38, based on the contrast marker 44 serving as an indicator.

As illustrated in FIGS. 3 and 4, the balloon-type electrode catheter 1 includes an electrode 46 disposed on a surface of the balloon 4. The electrode 46 of the present embodiment is formed of a metal thin film layered on the surface of the balloon 4. In this case, the electrode 46 can be formed by applying conductive ink containing metal forming the electrode 46 to the surface of the balloon 4.

The electrode 46 extends from the connecting member 18 to the small diameter portion 38 via the distal end inclined portion 40. The electrode 46 includes an end portion 46a disposed closer to the proximal end than the small diameter portion 38 is. The end portion 46a of the present embodiment is disposed at the proximal end inclined portion 42. Thus, the electrode 46 extends across the inner joining portion 32, the distal end inflatable portion 30, and the constricted portion 28 of the balloon 4. An end portion of the electrode 46 proximate to the distal end of the catheter shaft 2 is connected to the connecting member 18. Thus, the lead wire 20 and the electrode 46 are electrically connected via the connecting member 18. A part of the electrode 46 of the present embodiment proximate to the connecting member 18 has a tubular shape with approximately the same diameter as the inner joining portion 32. A plurality of strip-shaped portions radially spread from the end portion of the tubular portion proximate to the distal end inflatable portion 30. The end portion 46a of each strip-shaped portion is positioned in the proximal end inclined portion 42.

Figure 5:
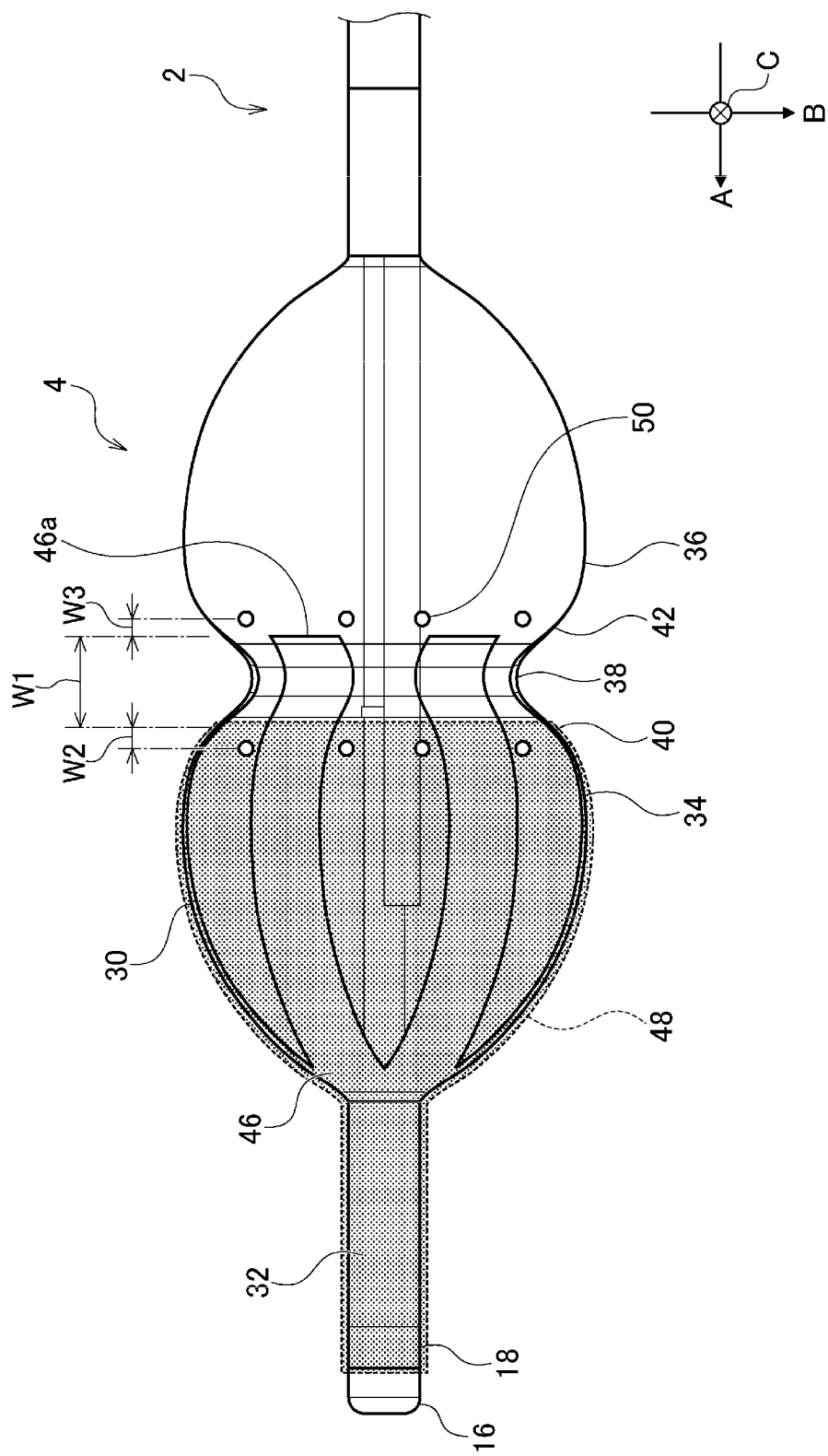
FIG. 5 is an enlarged side view of the part including the distal end of the balloon-type electrode catheter.

FIG. 5 is an enlarged side view of the distal end part of the balloon-type electrode catheter 1. The balloon-type electrode catheter 1 includes an insulating film 48. The insulating film 48 covers at least part of a region of the electrode 46 from the connecting member 18 to the distal end inclined portion 40. The electrode 46 is exposed at least in the small diameter portion 38, without being covered by the insulating film 48. As an example, the insulating film 48 can be formed by applying paint including a known insulating material to the surface of the electrode 46. The insulating film 48 of the present embodiment extends across the entire inner joining portion 32, the entire distal end inflatable portion 30, and part of the distal end inclined portion 40 of the balloon 4. Thus, the electrode 46 is exposed at the remaining part of the distal end inclined portion 40, the small diameter portion 38, and the proximal end inclined portion 42. A width W1 of the exposed portion of the electrode 46 in the axial direction of the catheter shaft 2, in other words, the width W1 from the proximal end portion of the insulating film 48 to the end portion 46a of the electrode 46 is, for example, from 1.5 mm to 4.5 mm.

The balloon 4 includes a through hole 50. The through hole 50 is a hole for communicating the inside and the outside of the balloon 4, and is used for discharging a fluid in the balloon 4 to the outside of the balloon 4. The through hole 50 can be formed by irradiating the balloon 4 with a laser beam or the like. The through hole 50 is disposed in at least one of the distal end inclined portion 40 or the proximal end inclined portion 42. Preferably, the through hole 50 is disposed in at least the distal end inclined portion 40. More preferably, the through hole 50 is disposed in both the distal end inclined portion 40 and the proximal end inclined portion 42. In the present embodiment, the plurality of through holes 50 are provided in each of the distal end inclined portion 40 and the proximal end inclined portion 42.

The through holes 50 disposed in the distal end inclined portion 40 are at positions separated from the exposed portion of the electrode 46 by a distance W2 in the axial direction of the catheter shaft 2. The through holes 50 disposed in the proximal end inclined portion 42 are at positions separated from the exposed portion of the electrode 46 by a distance W3. The distances W2 and W3 are, for example, from 0.5 mm to 1.5 mm. Note that the distances W2 and W3 may be the same value or different values. The plurality of through holes 50 are arranged in each of the inclined portions at a predetermined interval in the circumferential direction of the balloon 4. As an example, the plurality of through holes 50 are arranged at an interval of 45° in the circumferential direction. The through holes 50 are disposed to avoid the electrode 46, that is, the through holes 50 are disposed not to overlap the electrode 46.

Figure 6A:
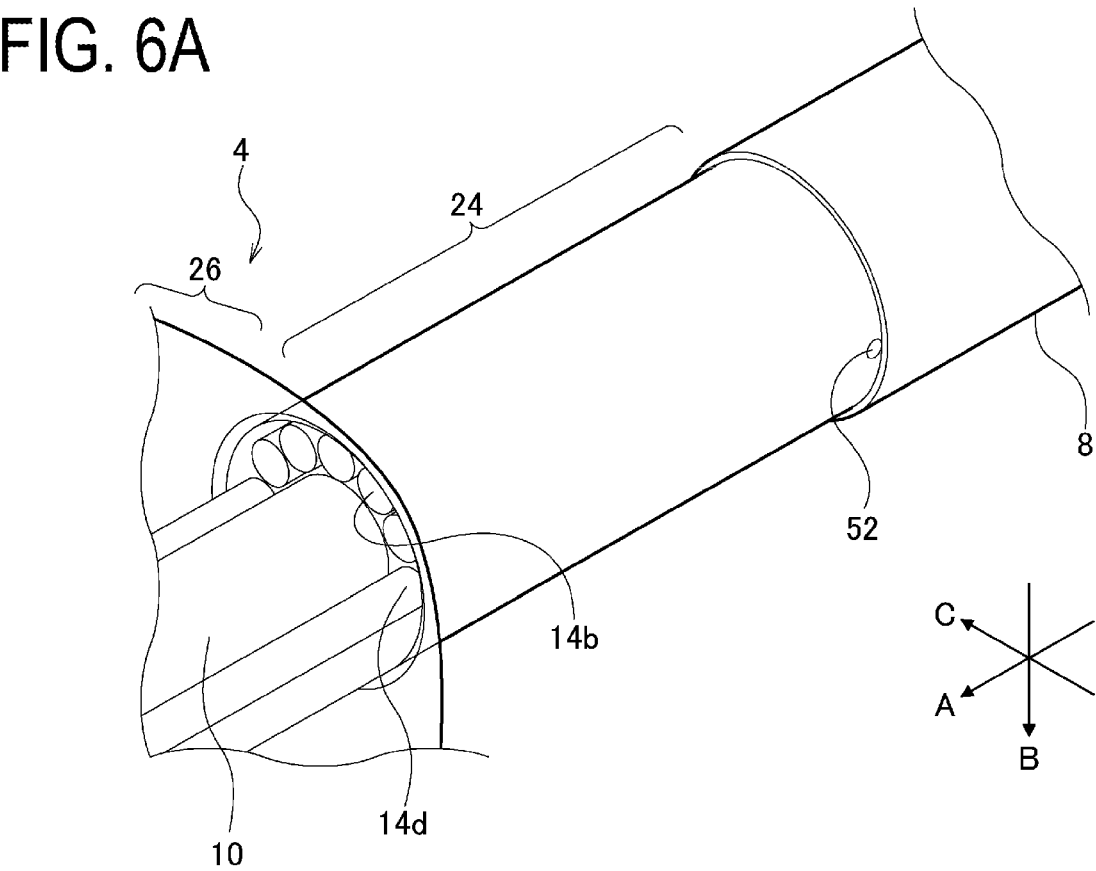
FIG. 6A is an enlarged perspective view of the part including the distal end of the balloon-type electrode catheter.
Figure 6B:
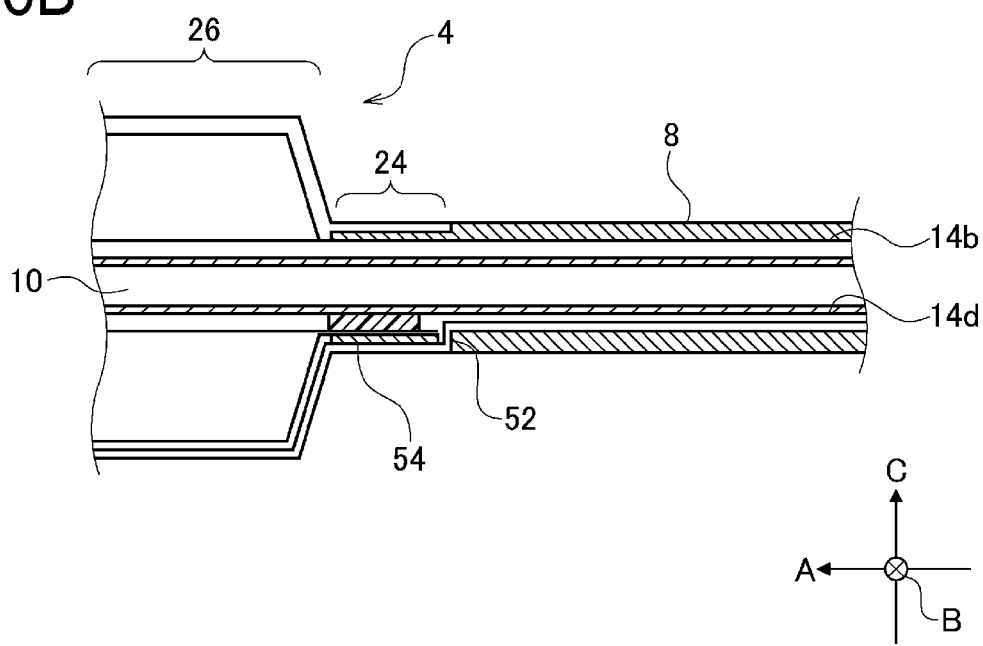
FIG. 6B is a schematic sectional view of the part including the distal end of the balloon-type electrode catheter.

FIG. 6A is an enlarged perspective view of the distal end part of the balloon-type electrode catheter 1. FIG. 6B is a schematic sectional view of the distal end part of the balloon-type electrode catheter 1. For convenience of explanation, some members are omitted in each of the drawings. As illustrated in FIGS. 6A and 6B, the outer shaft 8 includes a sensor through hole 52 for communicating the inside and the outside of the sensor lumen 14d, at a portion closer to the proximal end than the balloon 4 is. As an example, the sensor through hole 52 is provided at a position overlapping the outer joining portion 24.

The balloon-type electrode catheter 1 includes a temperature sensor 54 for measuring the temperature of the electrode 46. The temperature sensor 54 includes, for example, a thermocouple. The temperature sensor 54 extends from the proximal end part of the catheter shaft 2 to the sensor through hole 52 through the sensor lumen 14d. The temperature sensor 54 further extends through the sensor through hole 52 to reach the outer joining portion 24. The balloon 4 has a two-layer structure, and the temperature sensor 54 extends through a space between the layers of the balloon 4 to a position where the temperature of the electrode 46 can be measured. An opening of the sensor lumen 14d facing the inside of the balloon 4 is sealed with an adhesive or the like. The proximal end of the temperature sensor 54 is connected to an external control device via the handle 6.

Figure 7A:
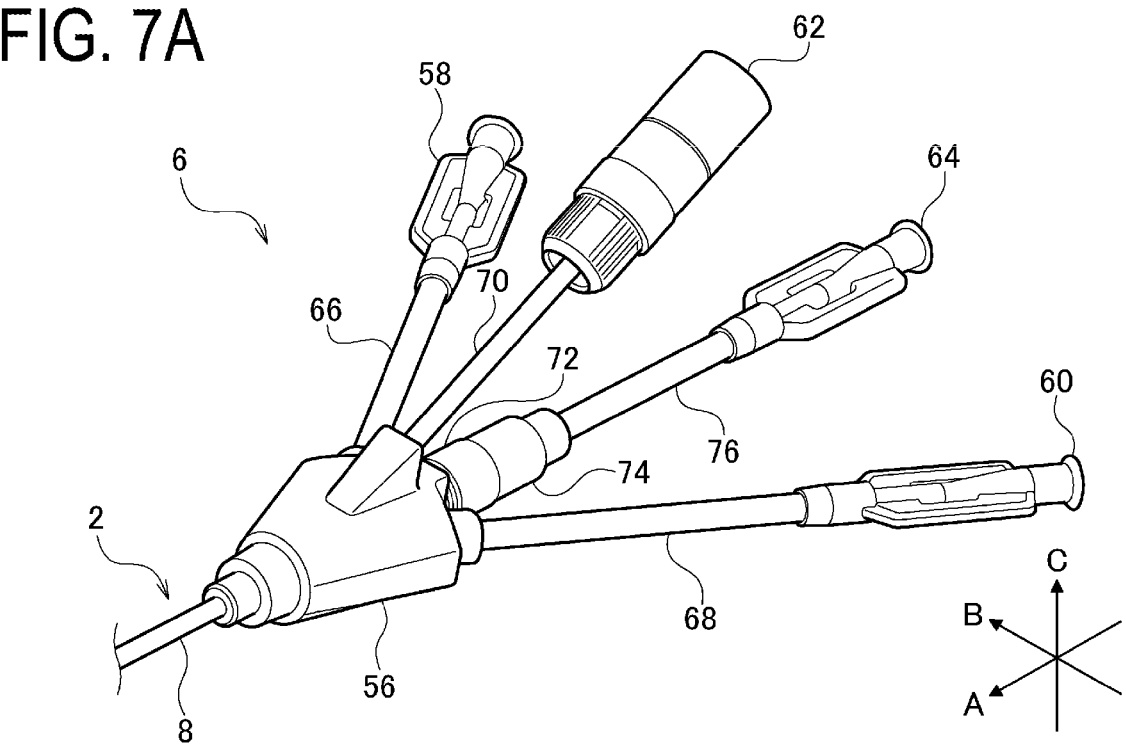
FIG. 7A is an enlarged perspective view of a part including a proximal end of the balloon-type electrode catheter.
Figure 7B:
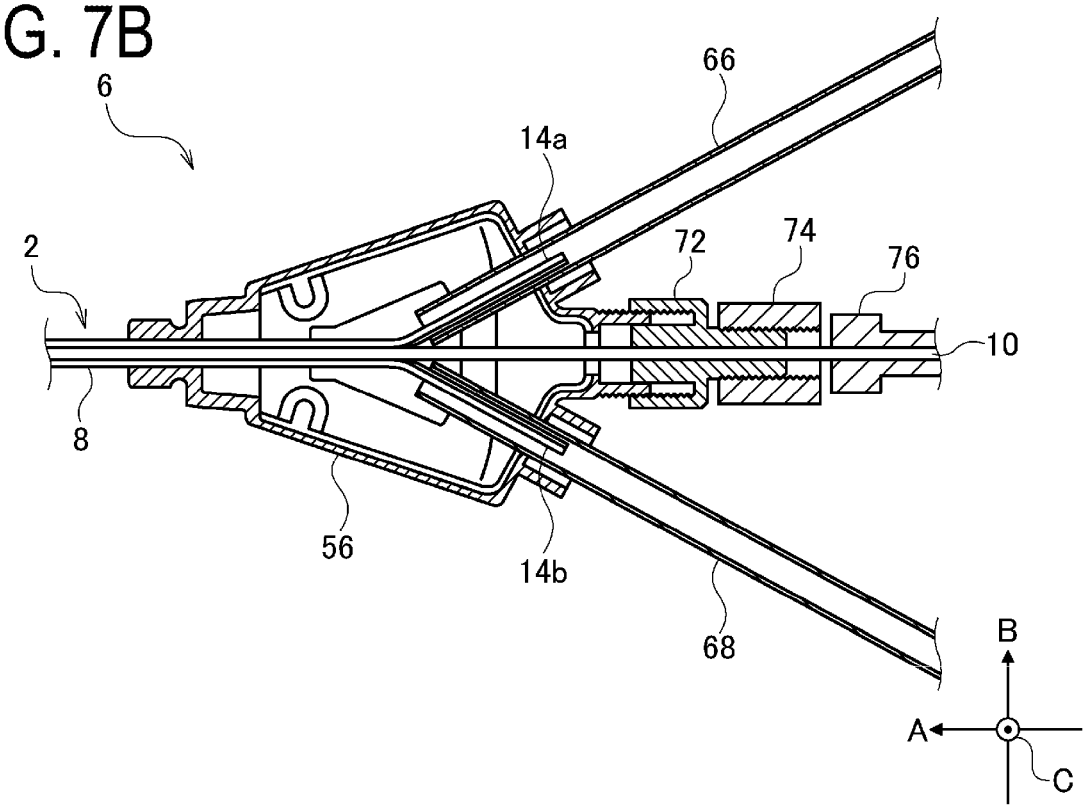
FIG. 7B is an enlarged sectional view of the part including the proximal end of the balloon-type electrode catheter.

FIG. 7A is an enlarged perspective view of the proximal end part of the balloon-type electrode catheter 1. FIG. 7B is an enlarged sectional view of the proximal end part of the balloon-type electrode catheter 1. The handle 6 includes a hub portion 56, a fluid port 58, an air port 60, a connector 62, and a guide wire port 64. The hub portion 56 is connected to the proximal end portion of the catheter shaft 2. In the hub portion 56, the supply lumen 14a, the discharge lumen 14b, the lead-wire lumen 14c, and the sensor lumen 14d are separately defined.

The fluid port 58 is connected to the hub portion 56 via a first protection tube 66. The first protection tube 66 includes one end connected to the fluid port 58 and the other end connected to the hub portion 56. The supply lumen 14a in the hub portion 56 is inserted in the first protection tube 66. Thus, the supply lumen 14a is connected to the fluid port 58 via the first protection tube 66. A connection portion between the first protection tube 66 and the supply lumen 14a is sealed by resin molding or the like.

The air port 60 is connected to the hub portion 56 via a second protection tube 68. The second protection tube 68 includes one end connected to the air port 60 and the other end connected to the hub portion 56. The discharge lumen 14b in the hub portion 56 is inserted in the second protection tube 68. Thus, the discharge lumen 14b is connected to the air port 60 via the second protection tube 68. A connection portion between the second protection tube 68 and the discharge lumen 14b is sealed by resin molding or the like.

The connector 62 is connected to the hub portion 56 via a third protection tube 70. The third protection tube 70 includes one end connected to the connector 62 and the other end connected to the hub portion 56. The lead wire 20 extending from the lead-wire lumen 14c and the temperature sensor 54 extending from the sensor lumen 14d in the hub portion 56 are inserted in the third protection tube 70, and are connected to a terminal incorporated in the connector 62. A connection portion between the third protection tube 70 and the lead-wire lumen 14c and the sensor lumen 14d is sealed by resin molding or the like.

The guide wire port 64 is connected to the proximal end portion of the inner shaft 10 protruding from the hub portion 56. A chuck member 72 having a tubular shape is fixed to an outlet of the inner shaft 10 in the hub portion 56. An operation ring 74 is attached to the chuck member 72. A screw groove is provided on the outer peripheral surface of the chuck member 72 and the inner peripheral surface of the operation ring 74, and the operation ring 74 is screwed with the chuck member 72. The operation ring 74 can be rotated to move toward and away from the hub portion 56. A support tube 76 that supports the inner shaft 10 is provided between the operation ring 74 and the guide wire port 64. The support tube 76 includes a through hole extending in the axial direction of the inner shaft 10, and the inner shaft 10 is inserted in this through hole. The support tube 76 and the inner shaft 10 are joined to each other.

The inner shaft 10 is not fixed to the hub portion 56, the chuck member 72, and the operation ring 74, and thus can be displaced with respect to these members. On the other hand, the outer shaft 8 is fixed to the hub portion 56 due to the coupling between the first protection tube 66 and the supply lumen 14a and the coupling between the second protection tube 68 and the discharge lumen 14b. When the operation ring 74 is displaced in a direction in which the operation ring 74 is away from the hub portion 56, the operation ring 74 presses the support tube 76 toward the proximal end. As a result, the inner shaft 10, together with the support tube 76, is displaced in a direction in which the inner shaft 10 is pulled out from the outer shaft 8. Note that the mechanism for displacing the inner shaft 10 is not limited to the one described above.

Next, a method of actuating the balloon-type electrode catheter 1 will be described. FIGS. 8A to 8C and FIG. 9 are diagrams for describing the method of actuating the balloon-type electrode catheter 1. For convenience of explanation, some members are omitted in each of the drawings. As an example, the balloon-type electrode catheter 1 can be used for a shunt surgery of forming a shunt S (through hole) in an atrial septum IAS.

First of all, preparation processing is executed before using the balloon-type electrode catheter 1. In the preparation processing, a fluid is supplied into the balloon 4 through the supply lumen 14a from the fluid port 58. In this processing, the air port 60 is in an open state. Part of the fluid supplied into the balloon 4 is discharged to the outside through the discharge lumen 14b and the air port 60, together with gas in the balloon 4 and the supply lumen 14a. After this air removal processing, the air port 60 is closed, and the fluid in the balloon 4 is discharged through the supply lumen 14a and the fluid port 58. As a result, the balloon 4 has a negative pressure, whereby the balloon 4 is folded.

Figure 8A:
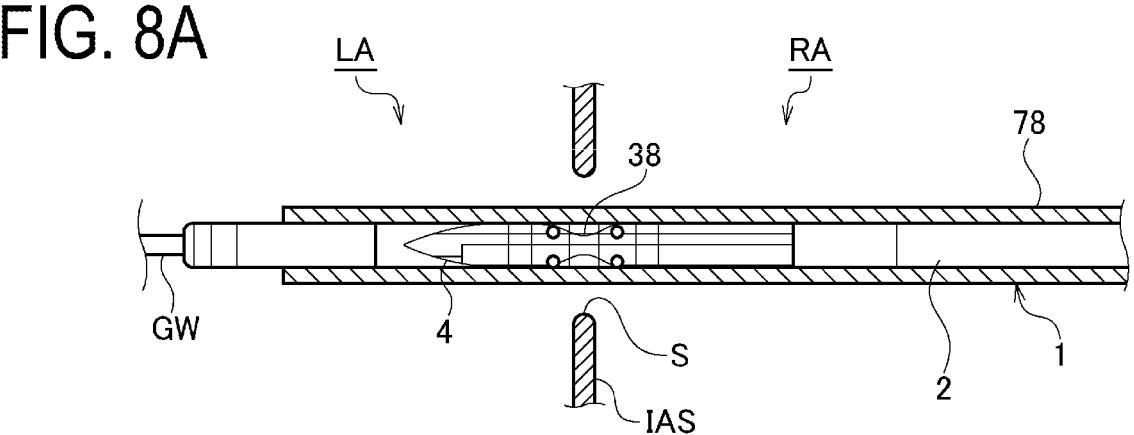
FIGS. 8A, 8B, and 8C are diagrams for describing a method of actuating the balloon-type electrode catheter.

As illustrated in FIG. 8A, the shunt S is provided at a treatment site of the atrial septum IAS through puncture using an RF needle or the like. Then, a sheath 78 passes through the shunt S after passing through the inferior vena cava and the right atrium RA. Subsequently, the guide wire GW is fed to the left atrium LA through the sheath 78. The balloon-type electrode catheter 1 is in a state in which the guide wire GW provided through the wire lumen 22. After the guide wire GW has reached the left atrium LA, the catheter shaft 2 is inserted into the body through the sheath 78. Then, the distal end portion of the catheter shaft 2 is fed to the left atrium LA along the guide wire GW. The balloon-type electrode catheter 1 is positioned such that the balloon 4 is inserted in the shunt S and the small diameter portion 38 overlaps with the shunt S. The practitioner can position the balloon-type electrode catheter 1, by checking the position of the contrast marker 44 with intracardiac echo (ICE), X-ray fluoroscopy, or the like.

Figure 8B:
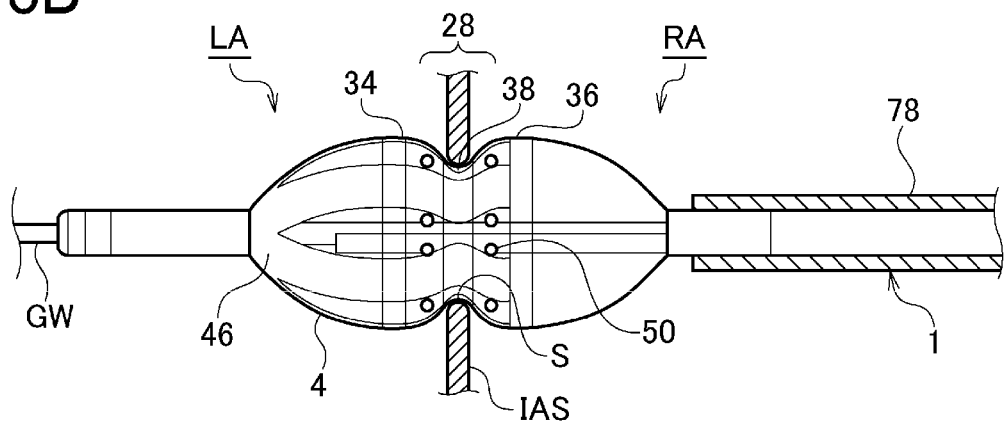

As illustrated in FIG. 8B, the sheath 78 is pulled out after the balloon 4 has reached the atrial septum IAS. As a result, the balloon 4 is exposed. With the balloon 4 exposed, a fluid is supplied from the fluid port 58 into balloon 4. Thus, the balloon 4 is inflated into a dumbbell shape. At this time, the air port 60 is in a closed state. When the balloon 4 is inflated, the peripheral edge portion of the shunt S fits in the constricted portion 28. As a result, the balloon 4 is fixed to the atrial septum IAS. The peripheral edge portion of the shunt S comes into contact with the electrode 46 exposed at the small diameter portion 38.

Figure 8C:
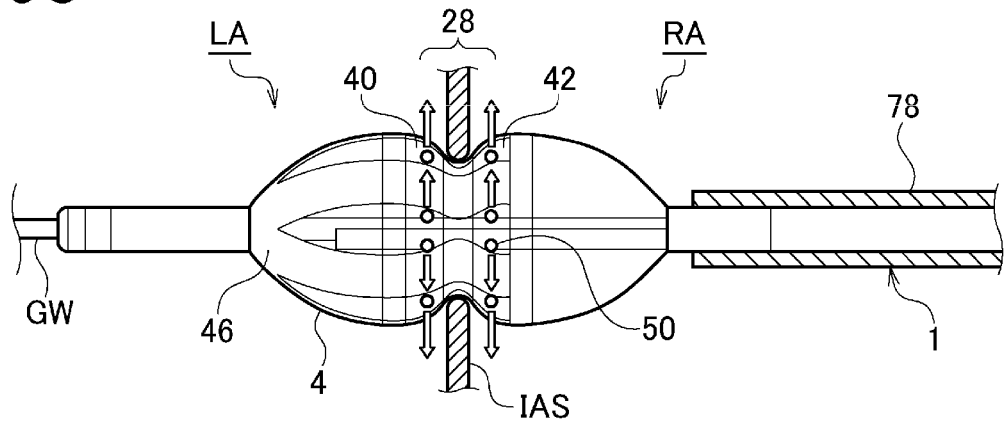

The balloon 4 includes the through holes 50. Thus, when the fluid flows into the balloon 4, the fluid is discharged through the through holes 50 as illustrated in FIG. 8C. In this manner, irrigation is implemented. The through holes 50 are provided in the distal end inclined portion 40 and the proximal end inclined portion 42. This facilitates a flow of the fluid in a gap between the constricted portion 28 and the atrial septum IAS. Thus, retention of the blood flow around the electrode 46 can be more effectively suppressed, whereby the formation of a thrombus due to the ablation can be suppressed.

A thrombus formed in the left atrium LA is likely to lead to a serious disease such as cerebral infarction, compared with a case where a thrombus is formed in the right atrium RA. Thus, it is more important to suppress the formation of a thrombus in the left atrium LA. In a typical shunt surgery, the distal end part of the balloon 4 is disposed in the left atrium LA, and the proximal end part of the balloon 4 is disposed in the right atrium RA. Thus, the through holes 50 are preferably provided in at least the distal end inclined portion 40 to be disposed in the left atrium LA. Thus, the formation of a thrombus in the left atrium LA can be more effectively suppressed.

When the through holes 50 are disposed in both the distal end inclined portion 40 and the proximal end inclined portion 42 as in the present embodiment, formation of a thrombus can be suppressed in both the left atrium LA and the right atrium RA. Thus, the safety of the shunt surgery can be further improved. Note that, as long as the through holes 50 are provided in at least one of the distal end inclined portion 40 or the proximal end inclined portion 42, at least the effect of suppressing thrombus formation can be achieved although it may not be fully exerted. In the present embodiment, the through holes 50 are disposed to avoid the electrode 46. Thus, excessive cooling of the electrode 46 due to the fluid flowing can be suppressed. Thus, the ablation can be more reliably performed.

Figure 9:
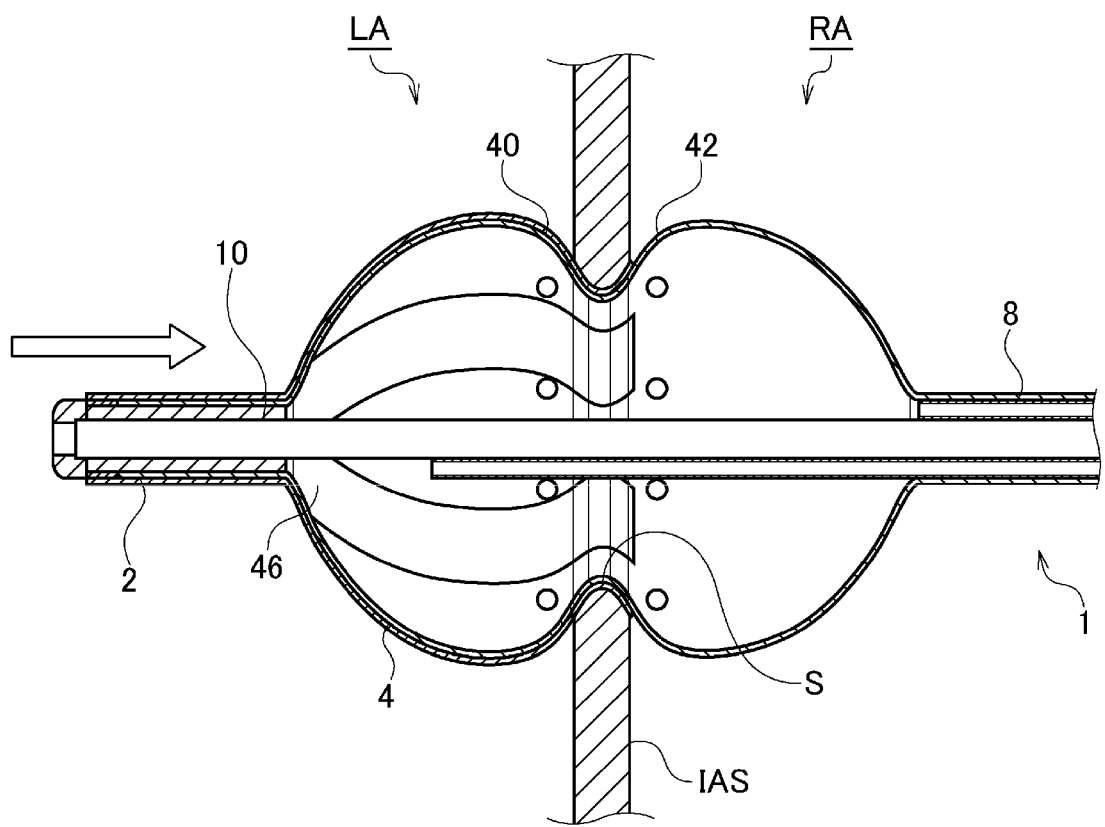
FIG. 9 is a diagram for describing the method of actuating the balloon-type electrode catheter.

Subsequently, the operation ring 74 is operated, resulting in relative displacement of the outer shaft 8 and the inner shaft 10 as illustrated in FIG. 9. In the present embodiment, the inner shaft 10 is displaced toward the proximal end of the balloon-type electrode catheter 1 with the outer shaft 8 serving as the fulcrum. As a result, the distal end portion and the proximal end portion of the balloon 4 are deformed to approach each other along the axial direction of the catheter shaft 2. As a result, the distal end inclined portion 40 and the proximal end inclined portion 42 approach each other, resulting in an increase in a contact area between the peripheral edge portion of the shunt S and the inclined portions. Thus, the contact area between the peripheral edge portion of the shunt S and the electrode 46 also increases.

In this state, ablation is executed with the electrode 46 energized with high-frequency current. With the ablation, the peripheral edge portion of the shunt S is thermally ablated. The thermal ablation denatures the peripheral edge portion of the shunt S, facilitating the preservation of the shunt S over a desired period of time. Note that thermal ablation may be performed using energy other than the high-frequency current.

By deforming the balloon 4 inflated by inflow of the fluid such that the balloon 4 is crushed in the axial direction of the catheter shaft 2, the peripheral edge portion of the shunt S can be sandwiched by the distal end inclined portion 40 and the proximal end inclined portion 42. Thus, the displacement of the electrode 46 during the ablation can be more effectively suppressed. Furthermore, the electrode 46 and the peripheral edge portion of the shunt S are more tightly brought into contact with each other, and thus high-frequency energy can be easily applied to the peripheral edge portion of the shunt S. Furthermore, the gap between the balloon 4 and the peripheral edge portion of the shunt S can be made small, whereby the retention of the blood and formation of a thrombus can be more effectively suppressed.

In the present embodiment, the inner joining portion 32 is disposed closer to the distal end of the catheter shaft 2 than the outer joining portion 24 is. The inner joining portion 32 approaches the outer joining portion 24, and thus the balloon 4 is deformed. In other words, the inner shaft 10 is displaced toward the proximal end with respect to the outer shaft 8, and thus the balloon 4 is shrunk in the axial direction of the catheter shaft 2. With this configuration, the balloon 4 can be deformed, while a load applied to the peripheral edge portion of the shunt S fitting in the constricted portion 28 is suppressed. Thus, the balloon 4 can be more easily deformed.

The inner shaft 10 of the present embodiment includes the distal end portion disposed closer to the distal end than the balloon 4 is, the distal end portion protruding from the outer shaft 8. The connecting member 18 is disposed at this distal end portion. The distal end portion of the inner shaft 10 exposed from the outer shaft 8 has a diameter reduced at least by an amount corresponding to the thickness of the outer shaft 8. Thus, by disposing the connecting member 18 at the distal end portion of the inner shaft 10, an increase in the diameter of the catheter shaft 2 due to provision of the connecting member 18 is suppressed.

Moreover, by disposing the connecting member 18 closer to the distal end than the balloon 4 is, the end portion 46a of the electrode 46 can be easily disposed closer to the proximal end than the small diameter portion 38 is. The portion of the balloon 4 closer to the proximal end than the small diameter portion 38 is disposed in the right atrium RA, and thus the end portion 46a of the electrode 46 is also disposed in the right atrium RA. Typically, the electrode 46 is likely to have a high temperature at the end portion 46a. Thus, by disposing the end portion 46a, which is likely to have a high temperature, in the right atrium RA, the formation of a thrombus in the left atrium LA can be more effectively suppressed. The balloon-type electrode catheter 1 of the present embodiment includes the insulating film 48 that covers at least part of the region of the electrode 46 from the connecting member 18 to the distal end inclined portion 40. The portion of the electrode 46 closer to the distal end than the small diameter portion 38 is disposed in the left atrium LA. Thus, the balloon-type electrode catheter 1 including the insulating film 48 can more effectively suppress the formation of a thrombus in the left atrium LA.

The catheter shaft 2 of the present embodiment includes the supply lumen 14a for causing a fluid to flow into the balloon 4 and the discharge lumen 14b for discharging the gas in the balloon 4. With this configuration, the discharging of the gas in the balloon 4 into the body through the through holes 50 can be suppressed. In addition, it is possible to suppress a phenomenon in which the gas inhibits contact between the electrode 46 and the fluid, the temperature of the electrode 46 locally increases, and progress of the ablation is inhibited. The supply port 14a1 of the supply lumen 14a is positioned closer to the distal end of the catheter shaft 2 than the discharge port 14b1 of the discharge lumen 14b is. This facilitates the discharging of the gas in the balloon 4.

The embodiment of the present disclosure has been described in detail. The embodiment described above is merely a specific example for carrying out the present disclosure. The content of the embodiment is not intended to limit the technical scope of the present disclosure. Many design changes such as changes, additions, and deletions of components can be made in the scope that does not depart from the spirit of the present disclosure specified in the claims. A new embodiment with design changes has effects of combined embodiments and variations thereof. In the embodiment described above, the content in which such design changes can be made has been emphasized with expressions such as "of the present embodiment" or "in the present embodiment", but design changes are also possible even in the content without such an expression. Any combination of components included in each embodiment is also effective as an aspect of the present disclosure. Hatching in sections of the drawings does not limit the material of a hatched object.

The embodiment may be identified by the items described below.

[Item 1]

A balloon-type electrode catheter (1) including
a catheter shaft (2) including an outer shaft (8) having a tubular shape and an inner shaft (10) housed in the outer shaft (8) in a state in which the inner shaft (10) is displaceable relative to the outer shaft (8) in an axial direction of the outer shaft (8), the catheter shaft (2) being insertable into a body,
a balloon (4) provided at a part including a distal end of the catheter shaft (2), the balloon (4) being inflatable with a fluid supplied from a part including a proximal end of the catheter shaft (2), and
an electrode (46) disposed on a surface of the balloon (4), wherein
the balloon (4) includes an outer joining portion (24) joined to the outer shaft (8) and an inner joining portion (32) joined to the inner shaft (10) at a position displaced from the outer joining portion (24) in the axial direction,
the balloon (4) in an inflated state includes a distal end large diameter portion (34), a proximal end large diameter portion (36) positioned closer to the proximal end of the catheter shaft (2) than the distal end large diameter portion (34) is, a small diameter portion (38) positioned between the distal end large diameter portion (34) and the proximal end large diameter portion (36) and being smaller in diameter than the two large diameter portions, a distal end inclined portion (40) connecting the distal end large diameter portion (34) and the small diameter portion (38), and a proximal end inclined portion (42) connecting the proximal end large diameter portion (36) and the small diameter portion (38),
the electrode (46) is exposed at at least the small diameter portion (38), and after the balloon (4) is inflated by inflow of the fluid, the outer shaft (8) and the inner shaft (10) are displaced relative to each other, and thus the balloon (4) deforms such that the distal end inclined portion (40) and the proximal end inclined portion (42) approach each other.

[Item 2]

The balloon-type electrode catheter (1) according to item 1, wherein the inner joining portion (32) is disposed closer to the distal end of the catheter shaft (2) than the outer joining portion (24) is, and the inner joining portion (32) approaches the outer joining portion (24) and thus the balloon (4) deforms.

[Item 3]

The balloon-type electrode catheter (1) according to item 1 or 2, including a lead wire (20) extending from the part including the proximal end of the catheter shaft (2) toward the part including the distal end of the catheter shaft (2), and a connecting member (18) disposed closer to the distal end of the catheter shaft (2) than the balloon (4) is, the connecting member (18) electrically connecting the lead wire (20) and the electrode (46), wherein the electrode (46) extends from the connecting member (18) to the small diameter portion (38) through the distal end inclined portion (40) and includes an end portion (46a) disposed closer to the proximal end of the catheter shaft (2) than the small diameter portion (38) is.

[Item 4]

The balloon-type electrode catheter (1) according to item 3, wherein the inner shaft (10) includes a distal end portion disposed closer to the distal end of the catheter shaft (2) than the balloon (4) is, the distal end portion protruding from the outer shaft (8), and the connecting member (18) is disposed at the distal end portion.

[Item 5]

The balloon-type electrode catheter (1) according to item 3 or 4, including an insulating film (48) covering at least part of a region of the electrode (46) from the connecting member (18) to the distal end inclined portion (40).

[Item 6]

The balloon-type electrode catheter (1) according to any one of items 1 to 5, wherein the catheter shaft (2) includes a supply lumen (14a) configured to cause the fluid to flow into the balloon (4) and a discharge lumen (14b) configured to discharge gas in the balloon (4).

[Item 7]

The balloon-type electrode catheter (1) according to item 6, wherein the supply lumen (14a) includes a supply port (14a1) in the balloon (4), the supply port (14a1) being configured to cause the fluid to flow into the balloon (4), the discharge lumen (14b) includes a discharge port (14b1) in the balloon (4), the discharge port (14b1) being configured to cause the gas to flow out of the balloon (4), and the supply port (14a1) is positioned closer to the distal end of the catheter shaft (2) than the discharge port (14b1) is.

[Item 8]

A method of actuating a balloon-type electrode catheter (1) including a balloon (4) provided with an electrode (46), the balloon (4) being provided at a part including a distal end of a catheter shaft (2), the method including causing a fluid to flow into the balloon (4) to inflate the balloon (4) in a dumbbell shape, deforming the balloon (4) such that a distal end portion (32) and a proximal end portion (24) of the balloon (4) approach each other along an axial direction of the catheter shaft (2), and energizing the electrode (46).

REFERENCE SIGNS LIST

1 Balloon-type electrode catheter
2 Catheter shaft
4 Balloon
8 Outer shaft
10 Inner shaft
14a Supply lumen
14a1 Supply port
14b Discharge lumen
14b1 Discharge port
18 Connecting member
20 Lead wire
24 Outer joining portion
28 Constricted portion
32 Inner joining portion
34 Distal end large diameter portion
36 Proximal end large diameter portion
38 Small diameter portion
40 Distal end inclined portion
42 Proximal end inclined portion
46 Electrode
46a End portion
48 Insulating film

The invention claimed is:

1. A balloon-type electrode catheter comprising:

a catheter shaft including an outer shaft having a tubular shape and an inner shaft housed in the outer shaft in a state in which the inner shaft is displaceable relative to the outer shaft in an axial direction of the outer shaft, the catheter shaft being insertable into a body;

a balloon provided at a part including a distal end of the catheter shaft, the balloon being inflatable with a fluid supplied from a part including a proximal end of the catheter shaft; and an electrode disposed on a surface of the balloon, wherein the balloon includes an outer joining portion joined to the outer shaft and an inner joining portion joined to the inner shaft at a position displaced from the outer joining portion in the axial direction, the balloon in an inflated state includes a distal end large diameter portion, a proximal end large diameter portion positioned closer to the proximal end of the catheter shaft than the distal end large diameter portion is, a small diameter portion positioned between the distal end large diameter portion and the proximal end large diameter portion and being smaller in diameter than the two large diameter portions, a distal end inclined portion connecting the distal end large diameter portion and the small diameter portion, and a proximal end inclined portion connecting the proximal end large diameter portion and the small diameter portion, the electrode is exposed at at least the small diameter portion, and after the balloon is inflated by inflow of the fluid, the outer shaft and the inner shaft are displaced relative to each other, and thus the balloon deforms such that the distal end inclined portion and the proximal end inclined portion approach each other.

2. The balloon-type electrode catheter according to claim 1, wherein the inner joining portion is disposed closer to the distal end of the catheter shaft than the outer joining portion is, and the inner joining portion approaches the outer joining portion and thus the balloon deforms.

3. The balloon-type electrode catheter according to claim 1, comprising:
   a lead wire extending from the part including the proximal end of the catheter shaft toward the part including the distal end of the catheter shaft; and
   a connecting member disposed closer to the distal end of the catheter shaft than the balloon is, the connecting member electrically connecting the lead wire and the electrode, wherein
   the electrode extends from the connecting member to the small diameter portion through the distal end inclined portion and includes an end portion disposed closer to the proximal end of the catheter shaft than the small diameter portion is.

4. The balloon-type electrode catheter according to claim 3, wherein
   the inner shaft includes a distal end portion disposed closer to the distal end of the catheter shaft than the balloon is, the distal end portion protruding from the outer shaft, and
   the connecting member is disposed at the distal end portion.

5. The balloon-type electrode catheter according to claim 3, comprising an insulating film covering at least part of a region of the electrode from the connecting member to the distal end inclined portion.

6. The balloon-type electrode catheter according to claim 1, wherein the catheter shaft includes a supply lumen configured to cause the fluid to flow into the balloon and a discharge lumen configured to discharge gas in the balloon.

7. The balloon-type electrode catheter according to claim 6, wherein
   the supply lumen includes a supply port in the balloon, the supply port being configured to cause the fluid to flow into the balloon,
   the discharge lumen includes a discharge port in the balloon, the discharge port being configured to cause the gas to flow out of the balloon, and
   the supply port is positioned closer to the distal end of the catheter shaft than the discharge port is.

8. A method of actuating a balloon-type electrode catheter including a balloon provided with an electrode, the balloon being provided at a part including a distal end of a catheter shaft, the method comprising:
   causing a fluid to flow into the balloon to inflate the balloon in a dumbbell shape;
   deforming the balloon such that a distal end portion and a proximal end portion of the balloon approach each other along an axial direction of the catheter shaft; and
   energizing the electrode.

* * * * *